(12) United States Patent
Topchik

(10) Patent No.: US 10,327,444 B2
(45) Date of Patent: Jun. 25, 2019

(54) SYSTEMS, METHODS, APPARATUS, MECHANISMS, AND DEVICES FOR DELIVERING ODORS, FRAGRANCES, AND CHEMICALS

(71) Applicant: Meryl J. Topchik, Boca Raton, FL (US)

(72) Inventor: Meryl J. Topchik, Boca Raton, FL (US)

( * ) Notice: Subject to any disclaimer, the term of this patent is extended or adjusted under 35 U.S.C. 154(b) by 0 days.

(21) Appl. No.: 16/102,453

(22) Filed: Aug. 13, 2018

(65) Prior Publication Data

US 2018/0360027 A1  Dec. 20, 2018

Related U.S. Application Data

(63) Continuation-in-part of application No. 15/864,543, filed on Jan. 8, 2018, now Pat. No. 10,076,114, which
(Continued)

(51) Int. Cl.
*A01N 25/08* (2006.01)
*B32B 7/05* (2019.01)
(Continued)

(52) U.S. Cl.
CPC ............ *A01N 25/08* (2013.01); *A01N 25/34* (2013.01); *A61K 8/0208* (2013.01); *A61K 8/0233* (2013.01); *A61Q 13/00* (2013.01); *A61Q 15/00* (2013.01); *B32B 1/02* (2013.01); *B32B 3/30* (2013.01); *B32B 5/142* (2013.01); *B32B 7/05* (2019.01); *B32B 7/12* (2013.01); *B32B 15/04* (2013.01); *B32B 15/08* (2013.01); *B32B 15/12* (2013.01); *B32B 15/20* (2013.01); *B32B 27/06* (2013.01); *B32B 29/002* (2013.01); *B32B 37/00* (2013.01); *B32B 37/12* (2013.01);
(Continued)

(58) Field of Classification Search
CPC .. A01N 25/08; B32B 7/05; B32B 3/30; B32B 1/02; B32B 5/142; B32B 15/08; B32B 27/06; B32B 15/12; B32B 29/002; B32B 37/00; B32B 15/04; B32B 7/12; B32B 15/20; B32B 37/12; B32B 2307/758; B32B 2439/40; B32B 2255/06; B32B 2307/764; B32B 2255/00; B32B 2307/414; B32B 2250/44; B32B 2264/102; B32B 2307/412; B32B 2264/06; B32B 2255/26; A61K 8/0208; A61K 8/0233; A61Q 13/00; A61Q 15/00
See application file for complete search history.

(56) References Cited

U.S. PATENT DOCUMENTS

| 4,771,935 A | 9/1988 | Hekal |
| 5,555,707 A | 9/1996 | Schwenger |
| 2013/0168270 A1 | 7/2013 | Koizumi et al. |

*Primary Examiner* — Trevor Love
(74) *Attorney, Agent, or Firm* — Jonathan A. Tyler

(57) ABSTRACT

A dispensing device includes a body having an open end, a second end, and a stick disposed in the body, the stick including a semi-solid material. The device also includes a mechanism adapted to cause a portion of the stick to extend from the open end of the body in response to an action by a user. The semi-solid material may include a deodorizing material, antiperspirant material, sanitizing material, perfume, sterilizing material, air freshening material, or insect repellent material. The stick may be uniformly composed of the semi-solid material, or may include a plurality of detachable blocks, each block including a layer of aluminum foil, a layer of adhesive material, and a layer of semi-solid material.

4 Claims, 15 Drawing Sheets

Related U.S. Application Data is a continuation of application No. 14/815,351, filed on Jul. 31, 2015, now Pat. No. 9,894,897.

(51) Int. Cl.
| | |
|---|---|
| *B32B 3/30* | (2006.01) |
| *B32B 1/02* | (2006.01) |
| *B32B 5/14* | (2006.01) |
| *B32B 15/08* | (2006.01) |
| *B32B 27/06* | (2006.01) |
| *A61K 8/02* | (2006.01) |
| *B32B 15/12* | (2006.01) |
| *A61Q 13/00* | (2006.01) |
| *A61Q 15/00* | (2006.01) |
| *B32B 29/00* | (2006.01) |
| *B32B 37/00* | (2006.01) |
| *A01N 25/34* | (2006.01) |
| *B32B 7/12* | (2006.01) |
| *B32B 15/20* | (2006.01) |
| *B32B 37/12* | (2006.01) |
| *B32B 15/04* | (2006.01) |

(52) U.S. Cl.
CPC ....... *B32B 2250/44* (2013.01); *B32B 2255/00* (2013.01); *B32B 2255/06* (2013.01); *B32B 2255/26* (2013.01); *B32B 2264/06* (2013.01); *B32B 2264/102* (2013.01); *B32B 2307/412* (2013.01); *B32B 2307/414* (2013.01); *B32B 2307/758* (2013.01); *B32B 2307/764* (2013.01); *B32B 2439/40* (2013.01)

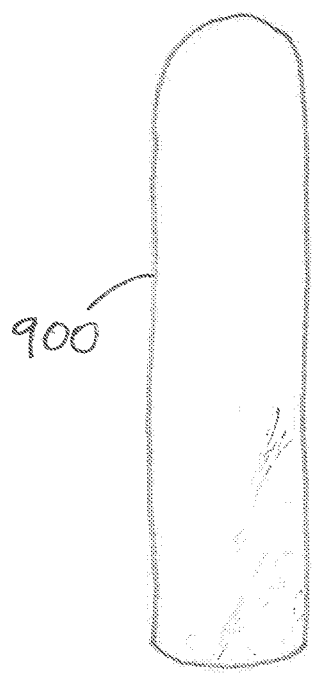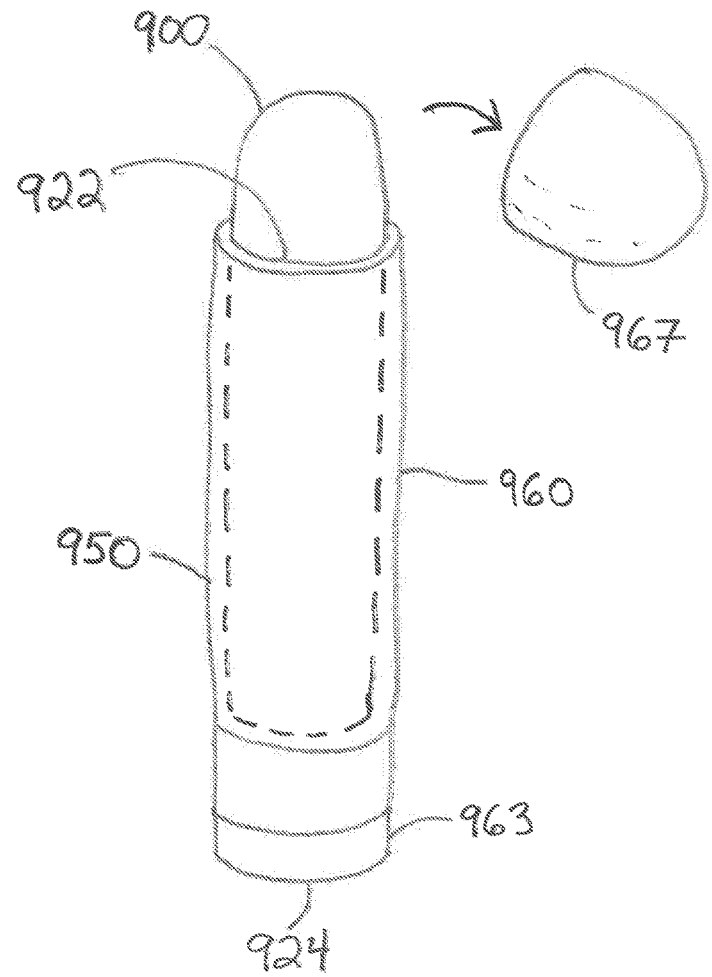
Fig. 9A
Fig. 9B

SYSTEMS, METHODS, APPARATUS, MECHANISMS, AND DEVICES FOR DELIVERING ODORS, FRAGRANCES, AND CHEMICALS

This application is a Continuation-in-Part of U.S. patent application Ser. No. 15/864,543, filed on Jan. 8, 2018, which is a Continuation of U.S. patent application Ser. No. 14/815,351, filed on Jul. 31, 2015, now issued as U.S. Pat. No. 9,894,897, issued on Feb. 20, 2018, each of which is incorporated by reference herein in its entirety for all purposes.

TECHNICAL FIELD

This Specification relates to systems, methods, apparatus, mechanisms, and devices for delivering odors, fragrances, and chemicals, including, without limitation, deodorizing blocks, deodorizing tape, and deodorizing sticks.

BACKGROUND

Many products exist to produce desired odors and fragrances, to mask an undesired odor, or to release a desired chemical into the air, including deodorants, antiperspirants, perfumes, air fresheners, insect repellents, etc. Deodorants and antiperspirants are often available as a stick made from a semi-solid material disposed in a hand-held tube. Perfumes are typically sold as liquids or sprayable fluids in hand-held bottles. Many air fresheners and insect repellents are sold in a can and are applied as a spray.

SUMMARY

In accordance with an embodiment, a block includes a first layer comprising a semi-solid material, and a second layer comprising an adhesive material, the second layer being attached to the first layer. The semi-solid material may include a deodorizing material, an antiperspirant material, a perfume-related substance, a sanitizing material, a sterilizing material, an air-freshening material, or an insect-repelling material.

In one embodiment, an item of manufacture includes a packaging adapted to hold the block. The packaging includes a first surface that includes a first material surrounding a region centrally located on the first surface, and a second material covering the region, the second material being attached to the first material. The packaging also includes a second surface opposite the first surface, the second surface including a third material covering at least a portion of the second surface that corresponds to the region, the third material being attached to the first material at least around a periphery of the region. The second material and the third material are separated by a volume. The block is disposed within the volume. The second layer of the block is removably attached to the third material.

In one embodiment, the second material is plastic.

In another embodiment, the third material is aluminum foil.

In another embodiment, the third material is adapted to break as a result of pressure exerted on the block.

In another embodiment, a product includes a plurality of the items of manufacture described above, wherein each of the items of manufacture is attached to at least a second one of the items of manufacture.

In accordance with another embodiment, a strip capable of being rolled into a roll is provided. The strip includes a first layer comprising a semi-solid material, and a second layer comprising an adhesive material, the second layer being attached to the first layer.

In one embodiment, the strip includes a strip of a selected material, and a plurality of blocks attached to the strip at regular intervals, each block comprising a first layer comprising a semi-solid material and a second layer comprising an adhesive material, the second layer being attached to the first layer.

In another embodiment, the strip includes a plurality of sections separated by respective perforations, each section comprising a respective one of the plurality of blocks.

In another embodiment, the semi-solid material includes a deodorizing material, an antiperspirant material, a perfume-related substance, a sanitizing material, a sterilizing material, an air-freshening material, or an insect-repelling material.

In another embodiment, an apparatus includes a tape dispenser adapted to hold a roll of a selected material, and a roll of the strip described above, wherein the roll is disposed in the tape dispenser.

In accordance with another embodiment, a stick includes a plurality of blocks detachably attached end-to-end, each block including a first layer comprising a semi-solid material, a second layer comprising an adhesive material, and a third layer comprising aluminum foil.

In one embodiment, the apparatus includes a cylindrical housing having an open end, the cylindrical housing having a size sufficient to hold the stick, a cap adapted to cover the open end, and a mechanism adapted to cause an end of the stick to exit the cylindrical housing via the open end.

In another embodiment, the semi-solid material includes a deodorizing material, an antiperspirant material, a perfume-related substance, a sanitizing material, a sterilizing material, an air-freshening material, or an insect-repelling material.

In accordance with another embodiment, a dispensing device is provided. The dispensing device includes a body having an open end, a second end, and an internal volume, a stick disposed in the internal volume of the body, the stick including a semi-solid material, and a mechanism adapted to cause a portion of the stick to extend from the open end of the body in response to an action by a user.

In one embodiment, the body has a cross-section having a shape selected from: a circle, an oval, a rectangle, a square, a triangle, and a star.

In another embodiment, the mechanism includes a first portion attached to the second end of the body of the dispensing device, the first portion being adapted to rotate, and a second portion disposed inside the internal volume, wherein rotation of the first portion causes the second portion to move within the internal volume and push the stick toward open end. By rotating the first portion, a user may cause a desired amount of the stick to extend from the open end of the dispensing device.

In another embodiment, the semi-solid material includes one of a deodorizing material, an antiperspirant material, a sanitizing material, a perfume, a sterilizing material, an air freshening material, and an insect repellent material.

In another embodiment, the dispensing device includes a cap adapted to attached to and cover the open end of the body.

In one embodiment, the stick is uniformly composed of a semi-solid material. In another embodiment, the stick includes a plurality of blocks, wherein each block includes a first layer of aluminum foil, a second layer of an adhesive material, and a third layer of a semi-solid material. Each block is removably attached to the stick.

These and other aspects of the present Invention will be more fully understood by reference to one of the following drawings.

BRIEF DESCRIPTION OF THE DRAWINGS

FIG. 9A shows a stick formed of a semi-solid material in accordance with an embodiment;

FIG. 9B shows a stick disposed in a stick container in accordance with an embodiment;

DETAILED DESCRIPTION OF THE INVENTION

Many products exist to produce desired fragrances, to mask an undesired odor, or to release a desired chemical into the air, including deodorants, antiperspirants perfumes, air fresheners, insect repellents, etc. Deodorants and antiperspirants are often available as a stick of a semi-solid material disposed in a hand-held tube. Perfumes are typically sold as liquids or sprayable fluids in hand-held bottles. Many air fresheners and insect repellents are sold in a can and are applied as a spray.

While many of these products are useful, in many circumstances the size and form of existing odor- and fragrance-related products are inconvenient or impractical. For example, a typical deodorant or antiperspirant stick is too bulky to be carried in a pocket; consequently, many people do not do so and as a result are able to apply deodorant or antiperspirant only once before leaving home for the day (or night). If an occasion then arises in which a deodorant or antiperspirant may be needed, the person often does not have access to a deodorant or antiperspirant, and must do without. Similarly, a typical can of air freshener or insect repellent is bulky and awkward; most people would not consider carrying around a container of air freshener or insect repellent in a purse or coat pocket. In some circumstances, existing products cannot be carried for other reasons. For example, due to security concerns, a bottle of air freshener, or a bottle of perfume, may not be permitted on an airplane.

Accordingly, a need exists for smaller, more convenient, and more discrete fragrance- and odor-related products to facilitate easier carrying and use of such products.

Figure 1A:
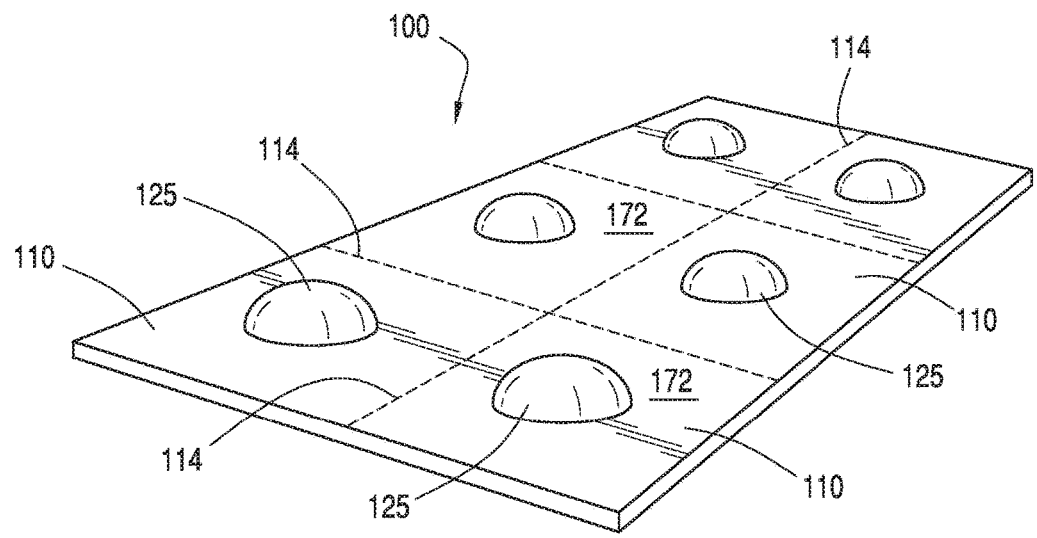
FIG. 1A shows a top view of a container in accordance with an embodiment.
Figure 1B:
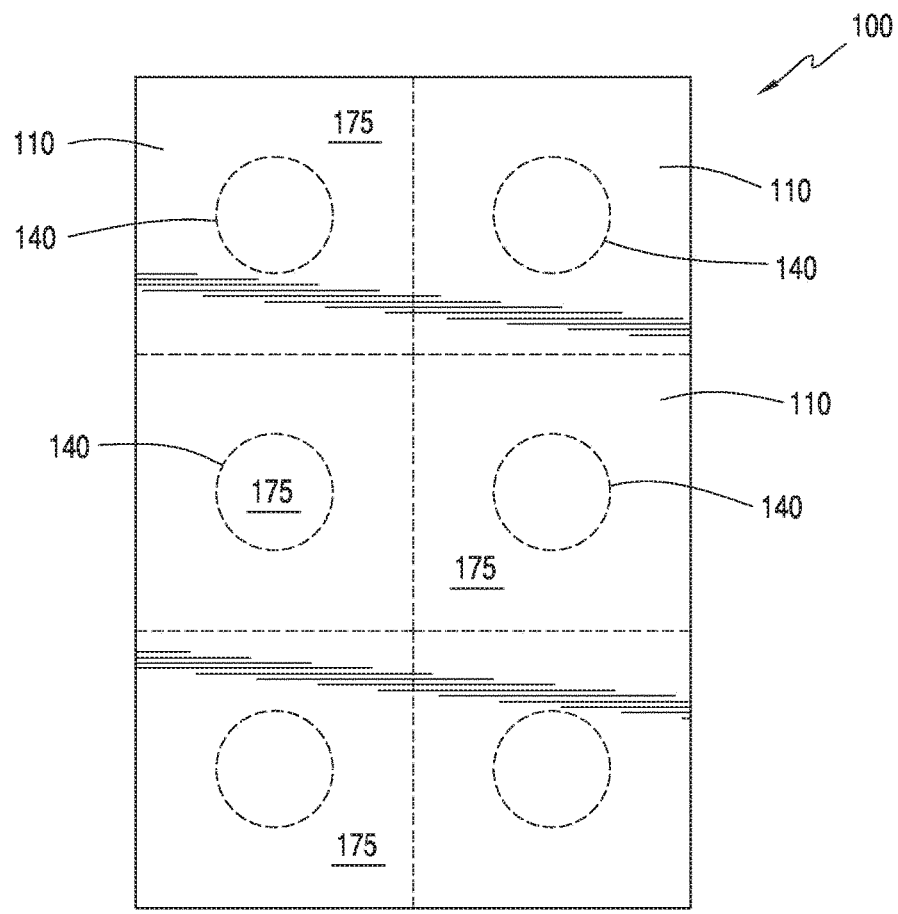
FIG. 1B shows a bottom view of the container of FIG. 1A.
Figure 1C:
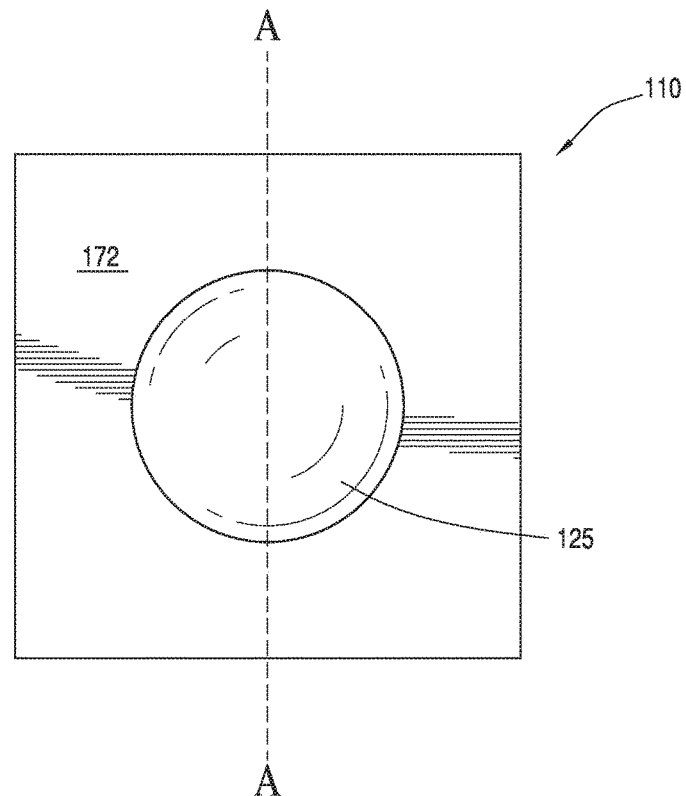
FIG. 1C shows a top view of a single section of the container of FIG. 1A.

FIGS. 1A-1C show a container in accordance with an embodiment. Container 100 is a packaging that holds a plurality of blocks each containing a material or chemical having a desired property such as a deodorant material, an antiperspirant material, a sanitizing material, a perfume, an insect repelling material, etc.

FIG. 1A shows a top view of block container 100 in accordance with an embodiment. Container 100 includes a plurality of sections 110 separated by perforated edges. In the illustrative embodiment, container 100 includes six container sections 110; however, in other embodiments, a container may contain any number of sections. The top surface of sections 110 is made of a suitable material 172, which may be paper, plastic, etc. Other materials may be used. Each individual section 110 may be detached from container 100 by tearing along its perforated edges 114. Each section 110 includes an enclosed volume 125. Each enclosed volume 125 is enclosed on the top side by a plastic material, which may be clear, translucent, or opaque. In other embodiments, enclosed volume 125 may be enclosed on the top side by another type of material, such as paper, foil, etc.

In one embodiment, enclosed volume 125 forms a circular or approximately circular shape less than 1.0 inch in diameter. In one embodiment, enclosed volume 125 forms a circular or approximately circular shape less than 0.5 inch in diameter. Enclosed volume 125 may have a different shape.

FIG. 1B shows a bottom view of container 100. The bottom surface of container 100 is covered by a layer 175 of aluminum foil. In other embodiments, layer 175 may include other materials. Each respective section 110 includes an outline 140 in the aluminum foil layer 175 that defines the bottom portion of the enclosed volume 125 of the respective section. Thus each enclosed volume 125 is sealed on the top side by a plastic material and on the bottom side by aluminum foil layer 175.

In one embodiment, outline 140 on bottom side of section 110 forms a circular or approximately circular shape less than 1.0 inch in diameter. In another embodiment, outline 140 on bottom side of section 110 forms a circular or approximately circular shape less than 0.5 inch in diameter.

Other dimensions may be used. In other embodiments, outline 140 may have a different shape, such as a square or rectangular shape.

In a well-known manner, outline 140 is adapted to break as a result of pressure. For example, outline 140 may be a perforation that facilitates breakage of the aluminum foil layer.

A user may detach a single container section 110 in order to facilitate the removal of a block. FIG. 1C shows a top view of a single container section 110. In one embodiment, each side of section 110 is between 0.5 inches long and 2 inches long. In another embodiment, each side of section 110 is approximately 1.0 inch long. Other dimensions may be used.

Material 172 (e.g., paper, plastic, etc.) surrounds and defines enclosed volume 125, which is situated in a region that is centrally located on section 110. In the illustrated embodiment, a plastic material covers the centrally located region and is attached to material 172, defining enclosed volume 125. Thus, material 172 surrounds enclosed volume 125.

Figure 1D:
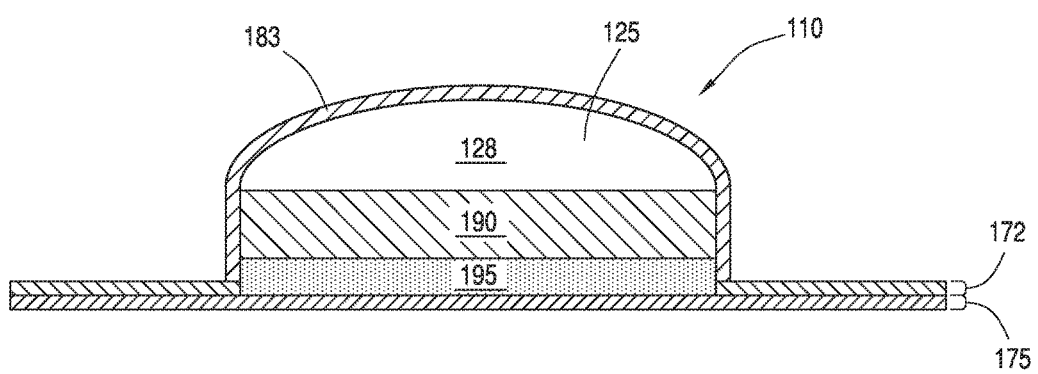
FIG. 1D shows a cross-section of the section shown in FIG. 1C.

FIG. 1D shows a cross-section of the section of FIG. 1C taken along line A. A layer of material 172 (e.g., paper, plastic, etc.) forms a base for the structure of section 110 and surrounds enclosed volume 125. A plastic material 183 covers enclosed volume 125. Plastic material 183 may be a clear plastic, or may be translucent, opaque, etc. Aluminum foil layer 175 covers the bottom of material 172 and seals the bottom of enclosed volume 125. Other materials may be used for any of the layers described herein.

In the illustrative embodiment, layer 172 is adjacent to and attached to aluminum foil layer 175. For example, layer 172 may be glued to layer 175. Plastic material 183 is attached to material 172, for example, by glue. In another embodiment, plastic material 183 is attached to aluminum foil layer 175.

Thus, layer 172, plastic material 183, and aluminum foil layer 175 define enclosed volume 125. Specifically, plastic material 183 is separated from aluminum foil layer 183 by enclosed volume 125.

In accordance with the illustrative embodiment, enclosed volume 125 holds a block that includes a plurality of layers. A first layer 190 includes a semi-solid material. A second layer 195 includes an adhesive material. A pocket 128 containing air, or another gas, may be located in between semi-solid layer 190 and plastic material 183. In other embodiments, a vacuum may be present between semi-solid layer 190 and plastic material 183.

In one embodiment, the diameter of the block is less than 1.0 inch long. In another embodiment, the diameter of the block is less than 0.5 inches long. In another embodiment, a block has a square shape; each side is less than 1.0 inch long. In one embodiment, the height of the block is less than 1.0 inch. In another embodiment, the height of the block is less than 0.5 inch. Other dimensions may be used.

In one embodiment, semi-solid layer 190 may be made from a material similar to those commonly used in deodorant/antiperspirant sticks. Thus, semi-solid layer 190 may include a gelling agent that forms a semi-solid matrix. The gelling agent may include a waxy or fatty material such as stearyl alcohol, cetyl alcohol, hydrogenated castor oil, glyceryl stearate, etc. The waxy or fatty material may be blended with an oil and emollient such as cyclomethicone. Cyclomethicone is a volatile silicone compound, and is a liquid at room temperature but quickly evaporates. In addition, talc, starches, and/or powders may be added to control the consistency of semi-solid layer 190. A fragrance, one or more fragrance-producing chemicals, or one or more chemicals that mask a fragrance, may be added. The fragrance or chemical(s) may be in a time-released form.

In the illustrative embodiment, semi-solid layer 190 comprises a deodorizing material or chemical; therefore, the discussion herein treats layer 190 as a deodorizing material. However, in other embodiments, semi-solid layer 190 may include an antiperspirant material or chemical, a perfume-related substance or chemical, a sanitizing material or chemical, a sterilizing material or chemical, an air-freshening material or chemical, an insect-repelling material or chemical, etc.

Adhesive layer 195 may include any suitable type of adhesive substance. Thus, adhesive layer 195 may include a drying adhesive, a pressure-sensitive adhesive, a contact adhesive, or another type of adhesive. For example, adhesive layer 195 may include an elastomer, such as an acrylic-based elastomer, a butyl rubber-based elastomer, etc. In other embodiments, adhesive layer 195 may include a glue or a paste.

Figure 2A:
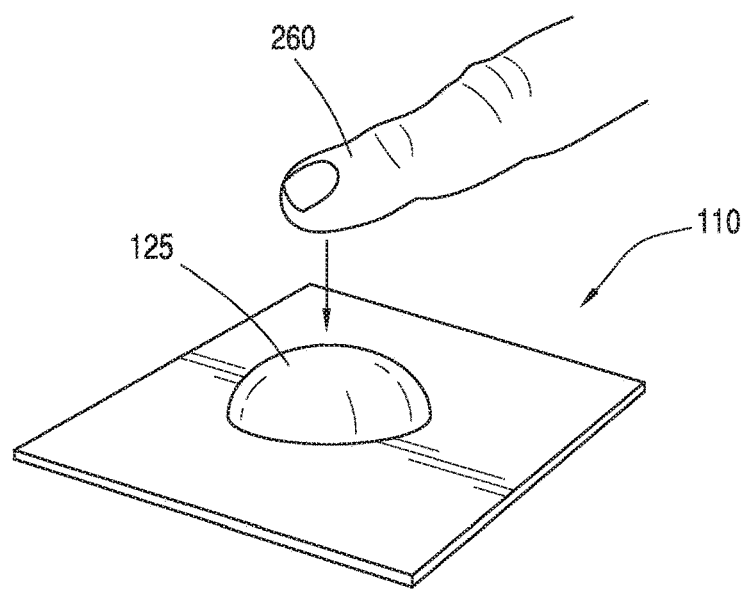
FIGS. 2A-2B illustrate a method of opening an individual section and removing a deodorizing block therefrom in accordance with an embodiment.
Figure 2B:
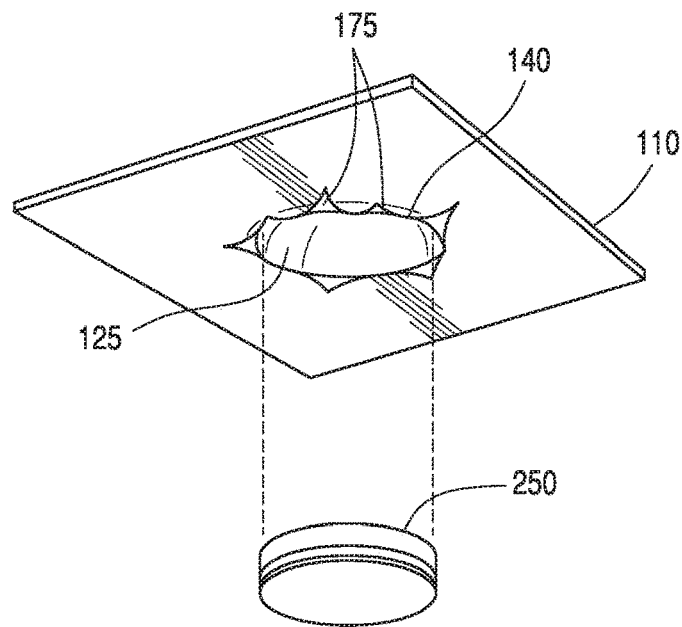

In accordance with an embodiment, a user may remove a block from the enclosed volume of a container section and use the block to deodorize a selected area (e.g., a room, a closet, a drawer, etc.), or part of the user's body. FIGS. 2A-2B illustrate a method of opening a section and removing a block therefrom in accordance with an embodiment. Referring to FIG. 2A, a user presses with a finger 260 on the top side of enclosed volume 125. The pressure from the user's finger 260 pushes onto the block 250 disposed within enclosed volume 125. Referring to FIG. 2B, when the user presses on the top side of the enclosed volume 125, the pressure from the user's finger 260 causes block 250 to press onto and through the aluminum foil layer 175 on the bottom side of section 110. The pressure causes the aluminum foil layer 175 to break along circular outline 140. After the aluminum foil layer 175 breaks along outline 140, block 250 can be removed from enclosed volume 125.

Figure 3A:
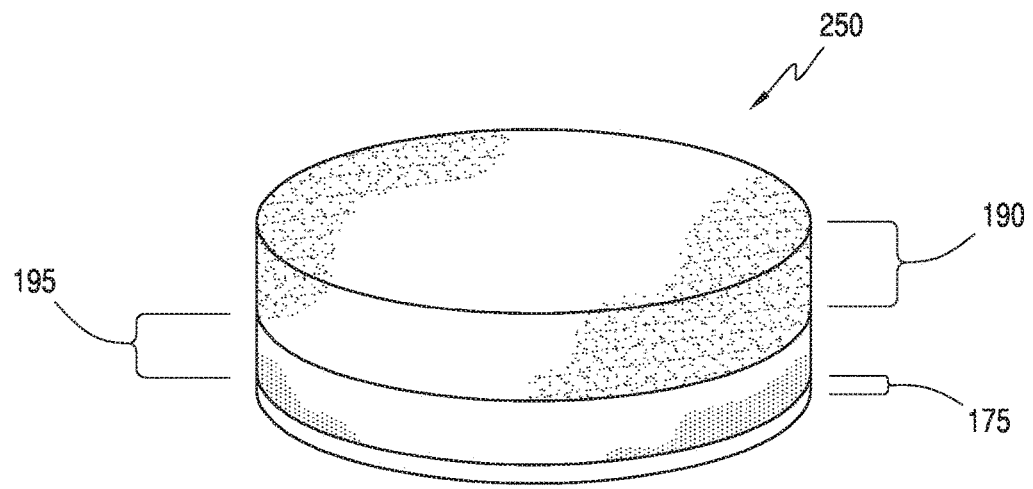
FIG. 3A shows a block in accordance with an embodiment.

FIG. 3A shows block 250 in accordance with an embodiment. Block 250 includes layer 190 and layer 195. Immediately after block 250 is removed from section 110, a layer of aluminum foil 175 remains attached to layer 195.

Figure 3B:
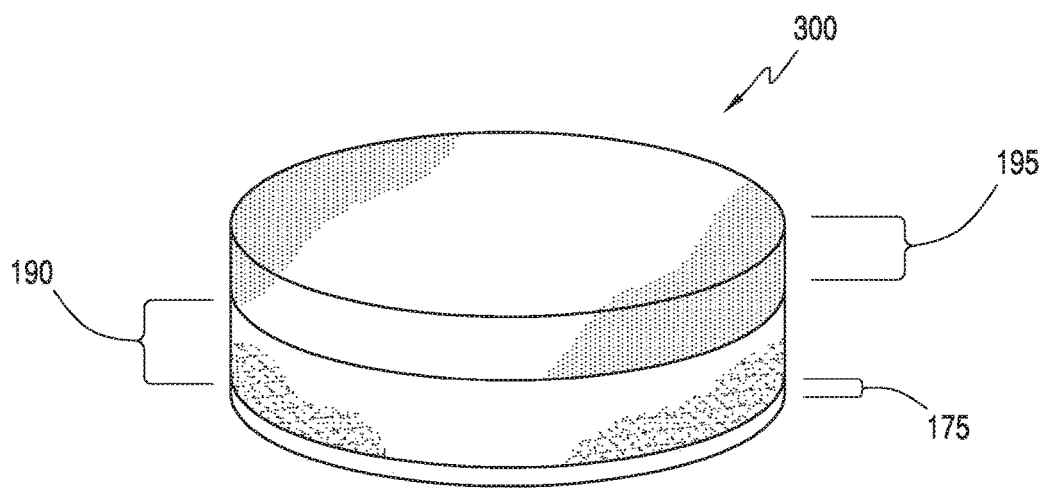
FIG. 3B shows a block in accordance with another embodiment.

FIG. 3B shows a block in accordance with another embodiment. Block 300 includes layers similar to those shown in FIG. 3A; however, semi-solid layer 190 is the middle layer. Adhesive layer 195 is adjacent to one side of layer 190, and aluminum foil layer 175 is adjacent to the opposite side of layer 190.

While the blocks shown in the Drawings are circular or approximately circular, blocks may have other shapes. Thus, blocks similar to those described herein may have an oval shape, a square shape, a rectangular shape, etc.

Figure 4A:
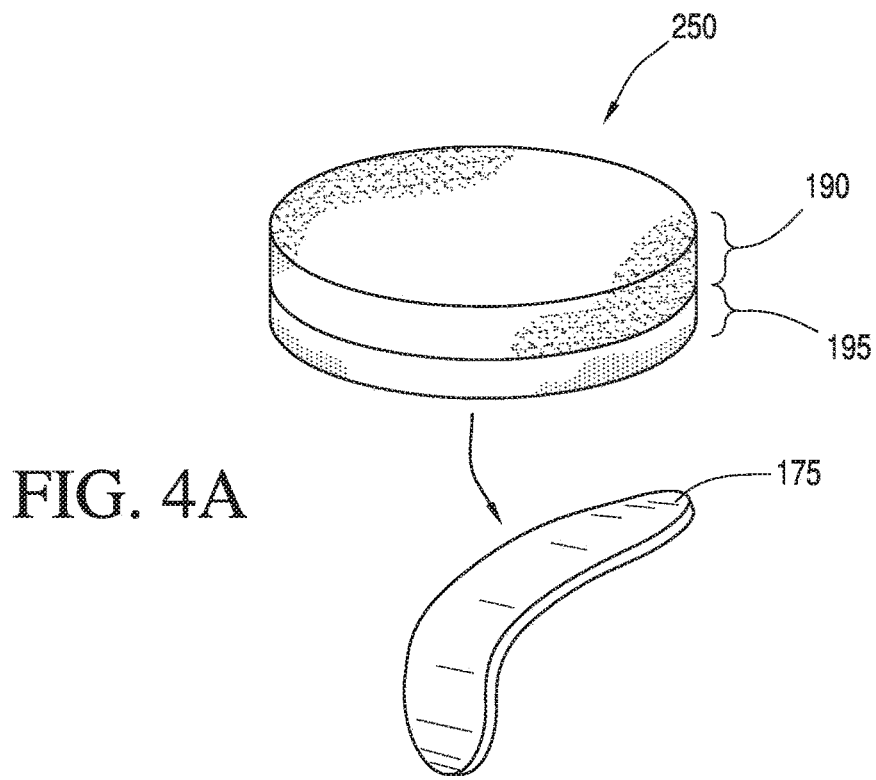
FIGS. 4A-4B show a method of attaching a block to a selected surface in accordance with an embodiment.
Figure 4B:
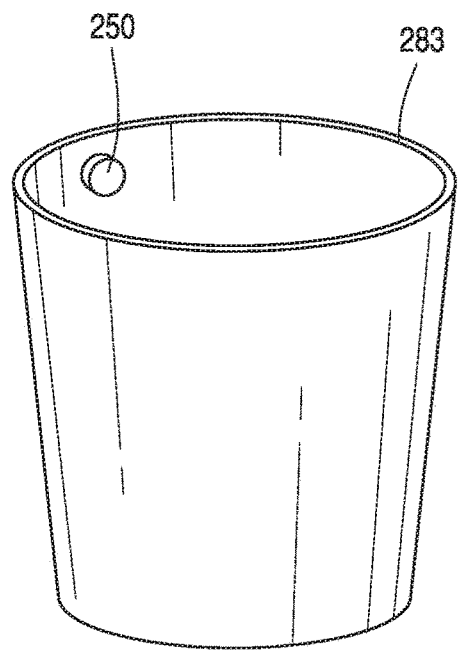
Figure 4C:
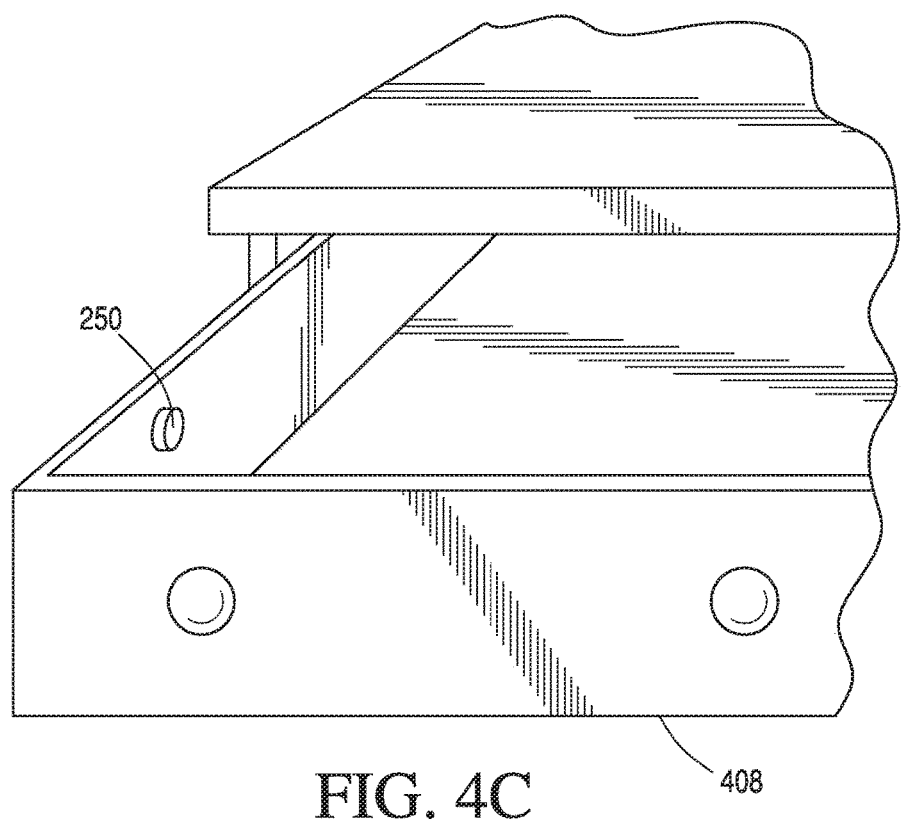
FIG. 4C shows a block attached to a surface of a drawer in accordance with an embodiment.

In accordance with an embodiment, a block may be attached to a selected surface and used to deodorize a selected location. FIGS. 4A-4B show a method of attaching a block to a selected surface in accordance with an embodiment. Referring to FIG. 4A, a user removes aluminum foil layer 175, exposing adhesive layer 195. The user may now stick block 250 onto a selected surface, using adhesive layer 195 to ensure that block 250 sticks to the surface. For example, the user may place the adhesive layer 195 of the block against the surface; the adhesive adheres to the surface, causing the block to remain in place. For example, a user may place block 250 on a surface inside the rim of a garbage can 283, as shown in FIG. 4B. After block 250 is attached to the inside surface of garbage can 283, deodorizing layer 190 is exposed to the air and begins to emit one or more chemicals or a deodorizing fragrance. For example, semi-solid layer 190 may emit one or more chemicals that mask the odors of garbage. Alternatively, semi-solid layer 190 may emit a desired fragrance. In another illustrative example, a user may place block 250 on an inside surface of a drawer 408, as shown in FIG. 4C. In this manner, the user may ensure that the drawer maintains a desired odor. In some embodiments, the semi-solid material of layer 190 gradually dissipates, disintegrates, or dissolves through exposure to the air.

In other embodiments, a block may be attached to other surfaces, such as a surface inside a drawer, a surface inside a suitcase or other item of luggage, a surface under a table, a surface in a bathroom, a surface in an automobile, etc.

In another embodiment, a block similar to those described herein may include semi-solid containing a material or chemical that may be placed or rubbed onto the skin or other part of the body, such as a deodorant material, an antiperspirant material, a perfume, an insect repellent, etc. In a manner similar to that described herein, a user may remove the block from a section 110 and touch or rub the semi-solid layer against his or her skin to cause some or all of the deodorant material, antiperspirant material, insect repelling material, or perfume to make contact with the skin. When a sufficient amount of the material or chemical contacts the skin and/or remains on the skin, the user may benefit from the odor-related properties of the material or chemical.

Because container 100 and sections 110 are relatively small in size and weight, a user may advantageously carry container 100, or one or more individual sections 110, in a pocket or purse and have quick access to a deodorant, an antiperspirant, an insect repellent, a perfume, etc.

Figure 5:
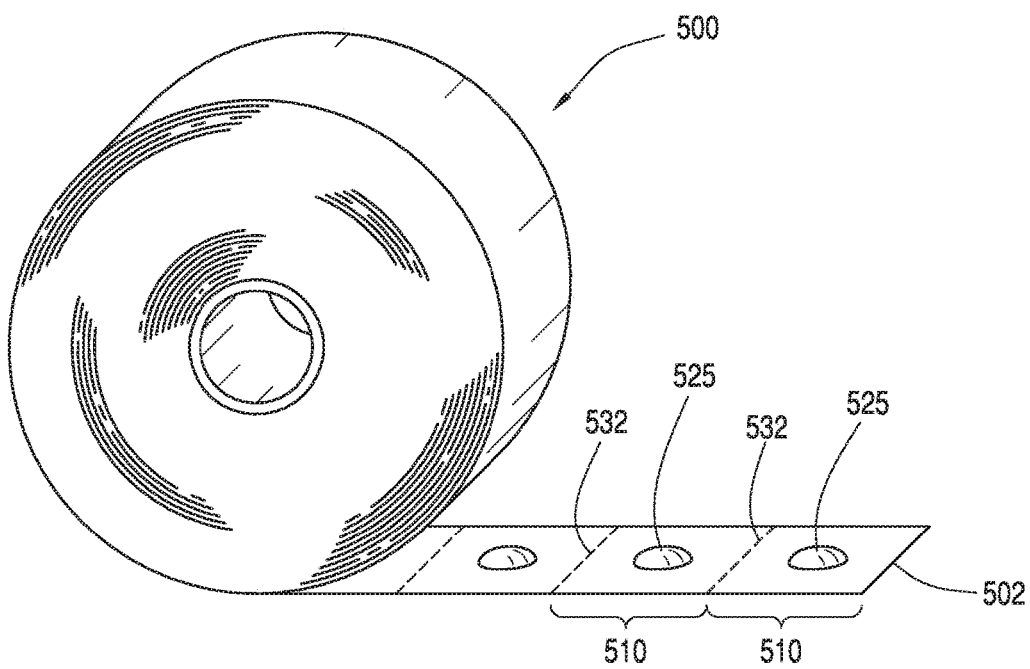
FIG. 5 shows a roll of roll sections in accordance with an embodiment.

In other embodiments, blocks similar to those shown in FIGS. 3A-3B and described with reference to FIGS. 3A-3B may be provided using other forms or within other forms of packaging. For example, sections holding blocks may be provided in a form similar to a roll of tape. FIG. 5 shows a roll 500 of roll sections in accordance with an embodiment. More particularly, a strip 502 includes a plurality of attached roll sections 510 that can be rolled into a compact roll 500. In one embodiment, roll sections 510 are of equal length; in other embodiments, roll sections may have different lengths. Each roll section 510 is connected to a succeeding roll section along a perforation 532. Roll 500 may be partially unrolled, and a single roll section 510 may be detached by tearing the section off along the perforation 532. In one embodiment, a single roll section is between 1.0 inch and 2.0 inches in length and less than 1.0 inch in width. Other dimensions may be used.

Figure 6A:
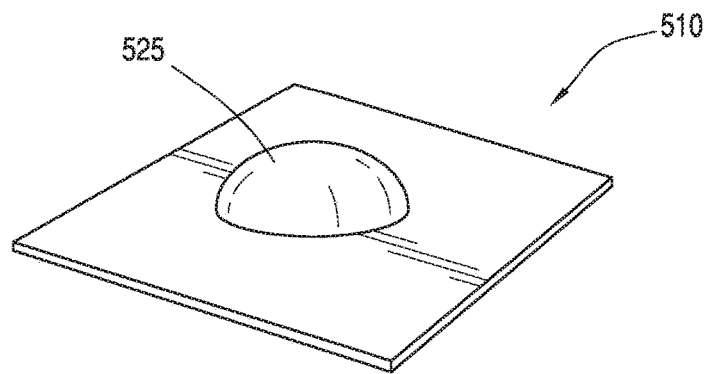
FIG. 6A shows a roll section in accordance with an embodiment.
Figure 6B:
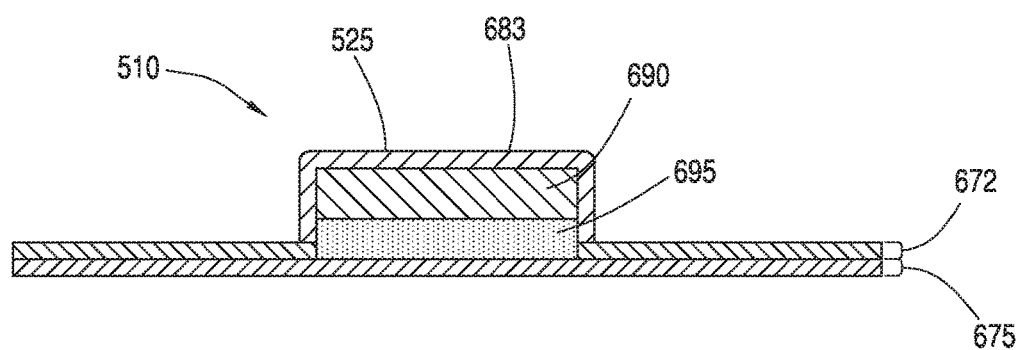
FIG. 6B shows a cross-section of the roll section of FIG. 6A.

FIG. 6A shows a roll section 510 in accordance with an embodiment. Roll section 510 is similar to a section 110 shown in FIGS. 1A-1C. Thus, roll section 510 includes an enclosed volume 525. FIG. 6B shows a cross-section of the roll section of FIG. 6A. Roll section 510 includes a base layer 672 of paper, plastic, or similar material which surrounds enclosed volume 525. A layer 675 of aluminum foil covers the bottom surface of roll section 510. The top side of enclosed volume 525 is sealed by a layer of plastic 683. Enclosed volume 525 contains a block that includes a semi-solid layer 690, which may be a deodorizing substance, for example, and an adhesive layer 695. In the illustrative example, plastic layer 683 is vacuum sealed around layers 690, 695; therefore, no pocket of air remains inside enclosed volume 525. In other embodiments, a pocket of air may remain inside enclosed volume 525.

A block made of layers 690, 695 may be removed from roll section 510 in a manner similar to that described in FIGS. 2A-2B. Therefore, a user may use a finger to push the block through the foil layer 675, peel off the foil layer that remain attached to adhesive layer 695, and place the block in a desired location.

Figure 6C:
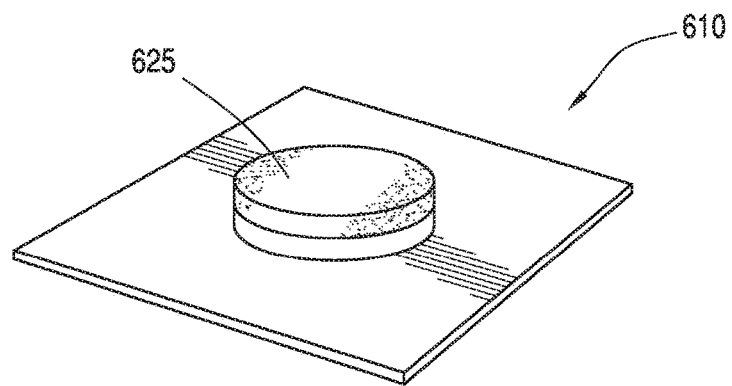
FIG. 6C shows a roll section in accordance with another embodiment.
Figure 6D:
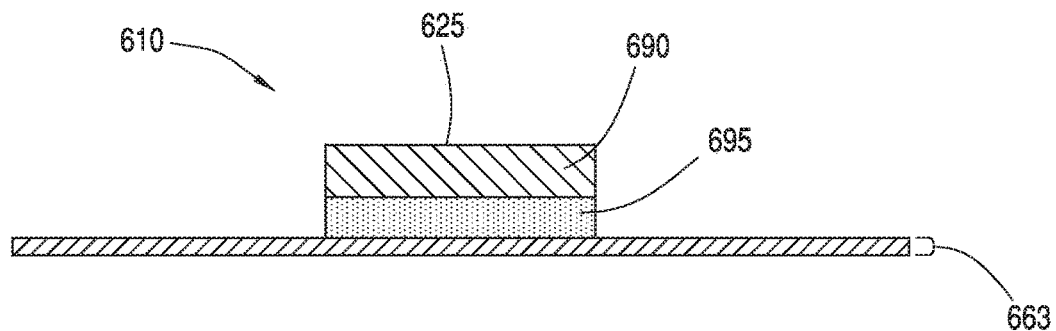
FIG. 6D shows a cross-section of the roll section of FIG. 6C.

In accordance with another embodiment, a roll includes a plurality of blocks 625 attached to a base layer at regular intervals (or at different intervals). FIG. 6C shows a cross-section of a roll section in accordance with an illustrative embodiment. Roll section 610 holds a block 625. Referring to FIG. 6D, roll section 610 includes a strip comprising a base layer 663, which may be paper, plastic, aluminum foil, or any other suitable material, and a block 625. Block 625 includes a semi-solid layer 690 and an adhesive layer 695; adhesive layer 695 is attached directly to layer 663. In this embodiment, block 625 is not covered by a plastic layer. Nevertheless, advantageously, semi-solid layer 690 is protected (and not exposed to air during storage) because the strip of sections is stored in the form of a roll; thus each block 625 is covered by another portion of the strip. Also advantageously, a user may use one or two fingers to remove block 625 directly from the top surface of section 610 by peeling block 625 away from layer 663. The user may then place block 625 in a desired location.

Figure 7A:
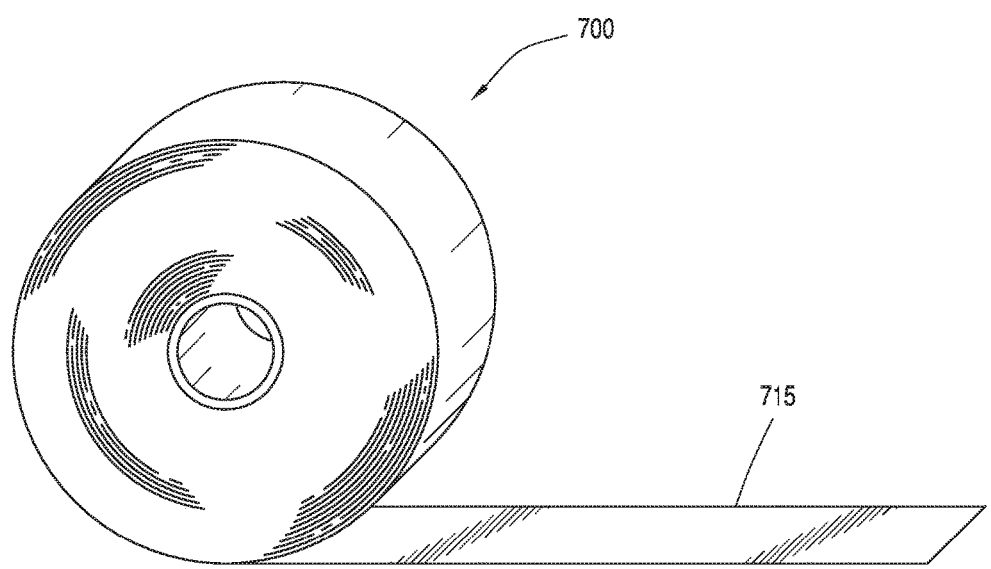
FIG. 7A shows a roll of tape in accordance with an embodiment.
Figure 7B:
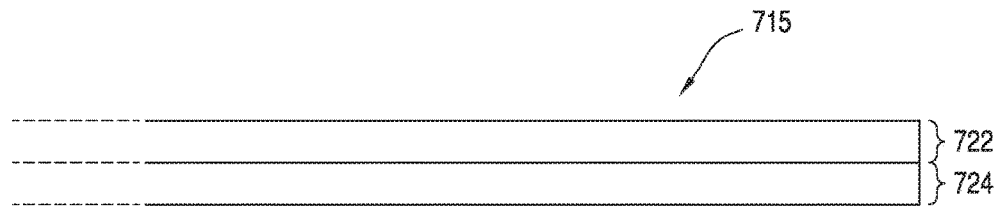
FIG. 7B shows a cross-section of the tape of FIG. 7A in accordance with an embodiment.
Figure 7C:
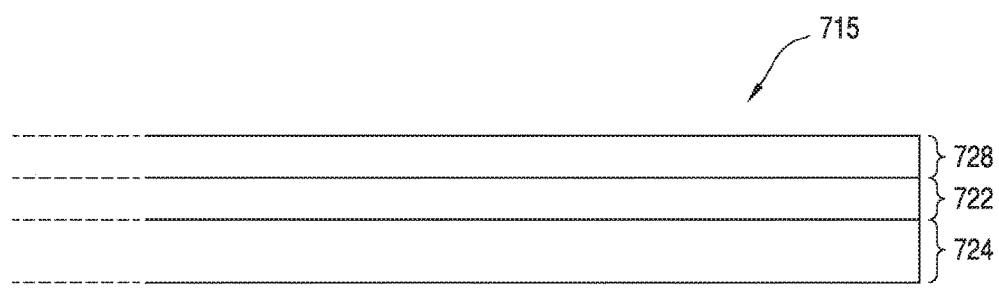
FIG. 7C shows a cross-section of tape in accordance with another embodiment.

In accordance with another embodiment, an odor-, fragrance- or chemical-releasing substance is provided in the form of an adhesive tape. FIG. 7A shows a roll of tape in accordance with an embodiment. Roll 700 includes a rolled strip of flexible tape 715. FIG. 7B shows a cross-section of tape 715 in accordance with an embodiment. Tape 715 includes a layer 722 of adhesive material and a layer 724 of a semi-solid material. For example, semi-solid layer 724 may include a deodorizing substance, an antiperspirant material, a sanitizing material, a perfume, a sterilizing material, an air freshening material, an insect repellent material, etc. Layer 722 is adjacent to and attached to layer 724. FIG. 7C shows a cross-section of tape 715 in accordance with another embodiment. Tape 715 includes a layer 722 of adhesive material and a layer 724 of a semi-solid material. In this embodiment, tape 715 also includes a layer 728 of aluminum foil. Thus, adhesive layer 722 is between and adjacent to semi-solid layer 724 and aluminum foil layer 728. Layers 722, 724, 728 may be configured in a different order than described herein. For example, a layer of semi-solid material may be disposed between an adhesive material and a layer of aluminum foil.

In accordance with an embodiment, a user may unroll a desired length of tape 715 and tear off, or cut off a piece of the tape with scissors, for example. If necessary, the user may remove the aluminum foil layer 728, and then attach the piece of tape to a selected surface, such as a surface on a trash can, a surface in a drawer, a surface in an automobile, etc. Adhesive layer 722 adheres to the selected surface and causes the piece of tape remain in place. While the piece adheres to the surface, semi-solid layer 724 releases a desired odor or chemical.

Figure 7D:
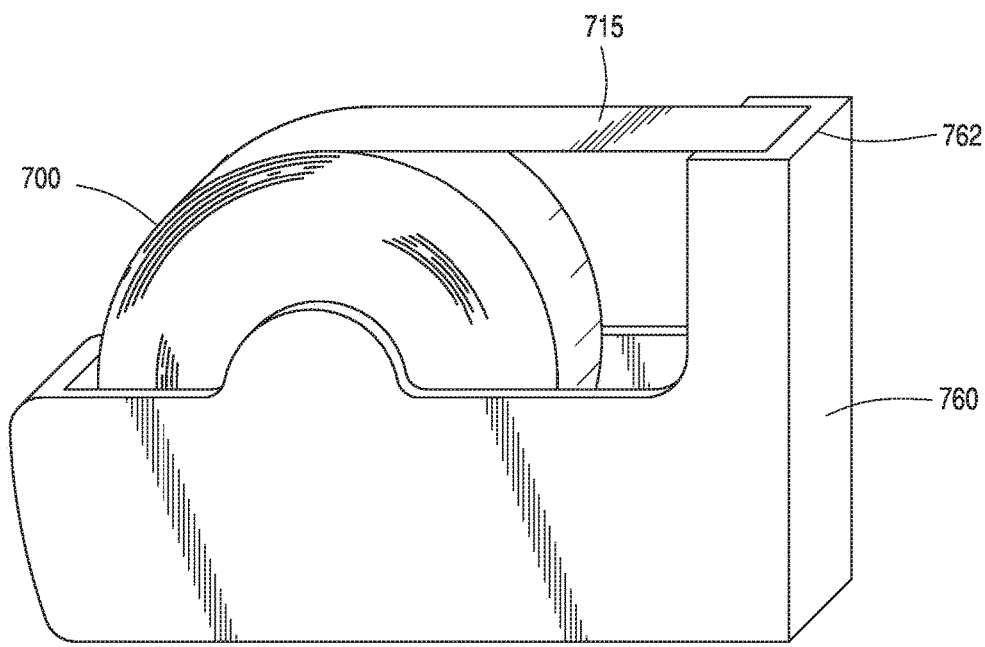
FIG. 7D shows the roll of the tape of FIG. 7A disposed in a tape dispenser.

In accordance with an embodiment, roll 700 may be stored in a dispenser similar to a tape dispenser, as shown in FIG. 7D. Dispenser 760 is similar to a well-known tape dispenser. Roll 700 is placed in dispenser 760. Tape 715 is unrolled and cut using a sharp edge 762 of dispenser 760, in a well-known manner.

Figures 8A, 8B:
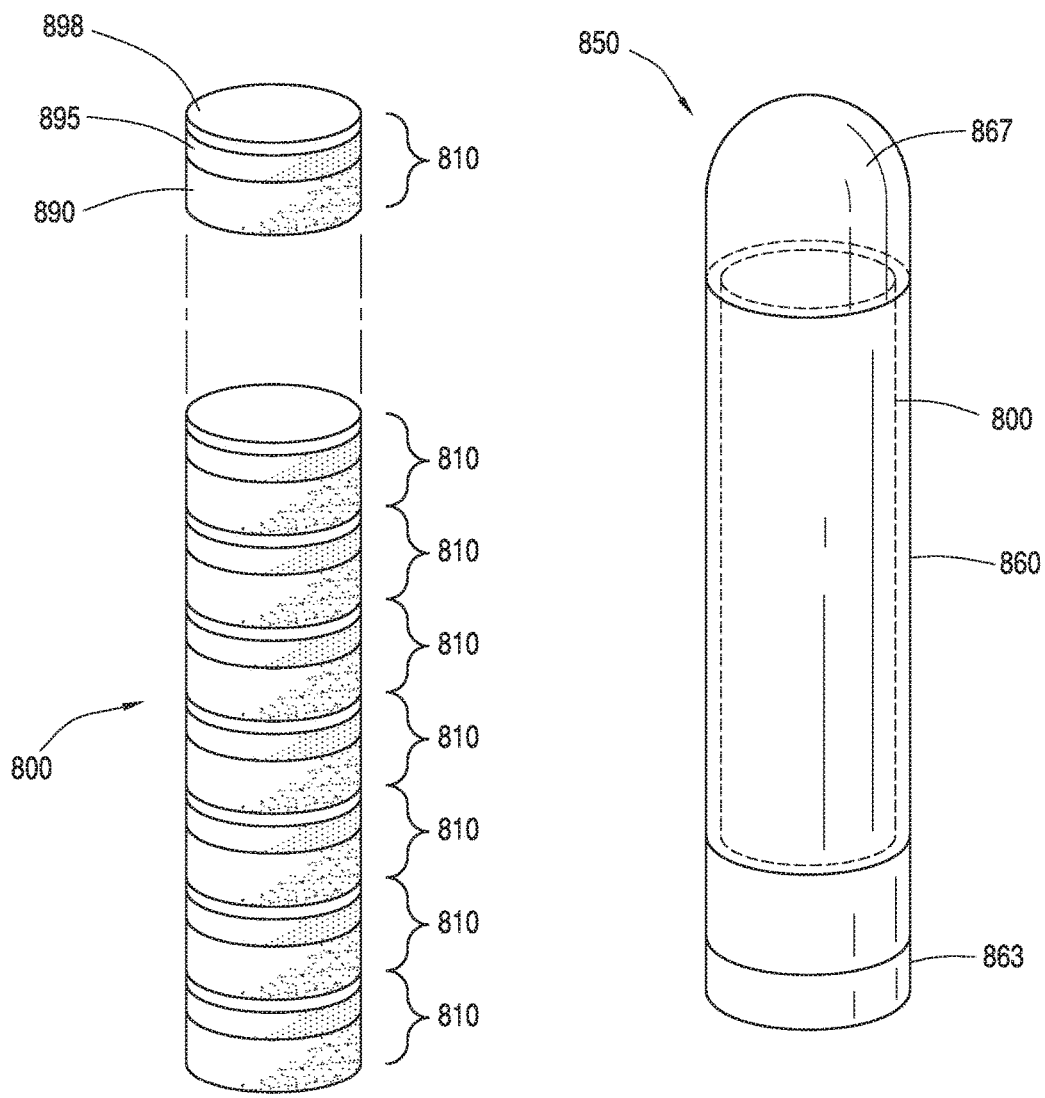
FIG. 8A shows a stick that includes a plurality of blocks in accordance with an embodiment.
FIG. 8B shows a container holding the stick of FIG. 8A in accordance with an embodiment.

In accordance with another embodiment, a plurality of blocks may be attached end-to-end to form a cylinder-shaped stick. FIG. 8A shows a stick 800 that includes a plurality of blocks 810 in accordance with an embodiment. Each block 810 includes a layer of semi-solid material and at least one additional layer of a second material different from the seme-solid material. In the illustrative embodiment, each block 810 includes a layer 898 of aluminum foil, a layer 895 of an adhesive material, and a layer 890 of a semi-solid material, which may include a deodorizing material, an antiperspirant material, a sanitizing material, a perfume, a sterilizing material, an air freshening material, an insect repellent material, etc. Each block 810 is removably attached to block 810. Thus each block is detachable from stick 800. A user may use one or several fingers to pull off or otherwise detach a single block 810 off the stick 800, as shown in FIG. 8A. In other embodiments, a block 810 may include other layers, or the layers 898, 895, 890 may be present in a different order than that shown in FIG. 8A. For example, a block may include a layer of a semi-solid, a layer of aluminum foil on one side of the semi-solid layer, and an adhesive layer on the opposite side of the semi-solid layer. In one embodiment, stick 800 may have a cylindrical shape and a circular cross-section. In other embodiments, a stick may have a different shaped cross-section.

For example, a stick may have a square, rectangular, oval, triangular, or star-shaped cross-section.

In accordance with an embodiment, stick 800 may be stored in a container such as that shown in FIG. 8B. Stick container 850 is similar to a well-known lipstick holding container. Thus, stick container 850 includes a cylindrical body 860, a cap 867, and a twisting mechanism 863. Cylindrical body 860 is at least partially hollow and includes an internal volume adapted to hold stick 800. Selected parts of stick container may be formed of plastic, for example.

Figure 8C:
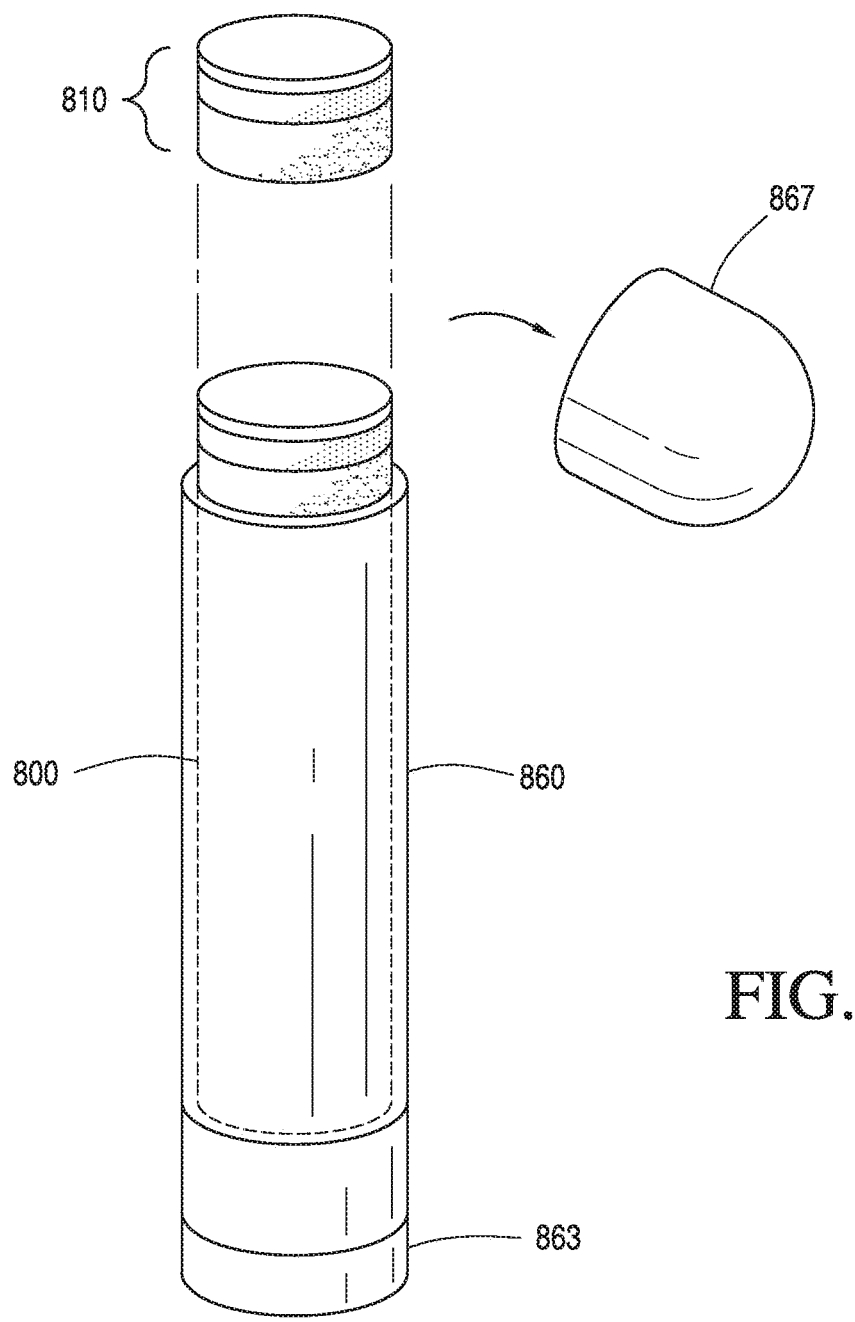
FIG. 8C shows the container of FIG. 8B holding the stick of FIG. 8A in accordance with an embodiment.

In one embodiment, twisting mechanism 863 includes a first portion that is attached to an end of cylindrical body 860 and adapted to rotate. In a well-known manner, a user may remove cap 867, as shown in FIG. 8C, and then rotate the rotating portion of twisting mechanism 863 to force one end of stick 800 to exit from cylindrical body 860. For example, a second portion of twisting mechanism 863 (shown in further detail in FIG. 9C) may be disposed within cylindrical body 860. Rotating the first portion of twisting mechanism 863 may cause the second portion inside the cylindrical body 860 to move within the cylindrical body and push stick 800 toward the opening of cylindrical body 860. As stick 800 moves, a portion of the stick extends from the open end of cylindrical body 860. After a sufficient length of stick 800 has emerged from the open end of cylindrical body 860, the user may use one or several fingers to pull off or otherwise detach a block 810. The user may then place block 810 in a selected location by placing the adhesive layer 895 against the surface, as discussed herein.

In other embodiments, other mechanisms may be used to cause stick 800 to exit or extend from the open end of cylindrical body 860. Other mechanisms may be used to allow a user to access and detach a block from stick 800. For example, in another embodiment, a user may push on the closed end of the body to cause stick 800 to move toward the open end. Other mechanisms may be used.

In accordance with another embodiment, a cylinder-shaped stick is uniformly formed of a semi-solid material, which may include, for example, a deodorizing material, an antiperspirant material, a sanitizing material, a perfume, a sterilizing material, an air freshening material, an insect repellent material, etc. In various embodiments, the stick may have a different shaped cross-sections, such as a circular, rectangular, triangular, oval shaped cross-section, etc.

The stick is disposed in a dispensing device (which may be cylindrical or have a different shape and/or cross-section). The dispensing device has at least one end that is open. A first portion of the stick is enclosed within the dispensing device while a second portion of the stick extends from the open end and is exposed. The dispensing device may include a removable cover adapted to cover the exposed portion of the stick.

The dispensing device is further adapted to allow a user to apply pressure, or perform an action such as twisting, on a selection part of the dispensing device, and thereby cause a selected length of the stick to be pushed out of the open end of the dispensing device. For example, the dispensing device may have a closed end opposite the open end, and allow the user to push the closed end to cause a desired length of the stick to extend from the open end. Alternatively, the dispensing device may include a twisting mechanism disposed at the close end. A user may twist the twisting mechanism; in response the twisting mechanism pushes a desired length of the stick from the open end of the dispensing device. Other mechanisms may be used to allow a user to access the stick.

FIG. 9A shows a stick 900 uniformly composed of a semi-solid material in accordance with an embodiment. For example, stick 900 may be formed of a deodorizing material, an antiperspirant material, a sanitizing material, a perfume, a sterilizing material, an air freshening material, an insect repellent material, etc.

In the illustrative embodiment, stick 900 has a circular cross-section. In other embodiments, a stick may have a different shaped cross-section. For example, a stick may have a square, rectangular, oval, triangular, or star-shaped cross-section.

In accordance with an embodiment, stick 900 may be stored in a stick container such as that shown in FIG. 9B. FIG. 9B shows a stick disposed in a stick container in accordance with an embodiment. Stick container 950 is similar to a well-known lipstick holding container. Thus, stick container 950 includes a cylindrical body 960, a cap 967, and a twisting mechanism 963. Cylindrical body 960 has an internal volume that is adapted to hold stick 900. In the illustrative embodiment, cylindrical body 960 has an open end 922 and a closed end 924. In other embodiments, a stick container may have other shapes, forms, and structures.

For example, a stick container may have a body with a cross-section having any desired shape such as, for example, and without limitation, a circle, oval, rectangle, square, triangle, or star.

Figure 9C:
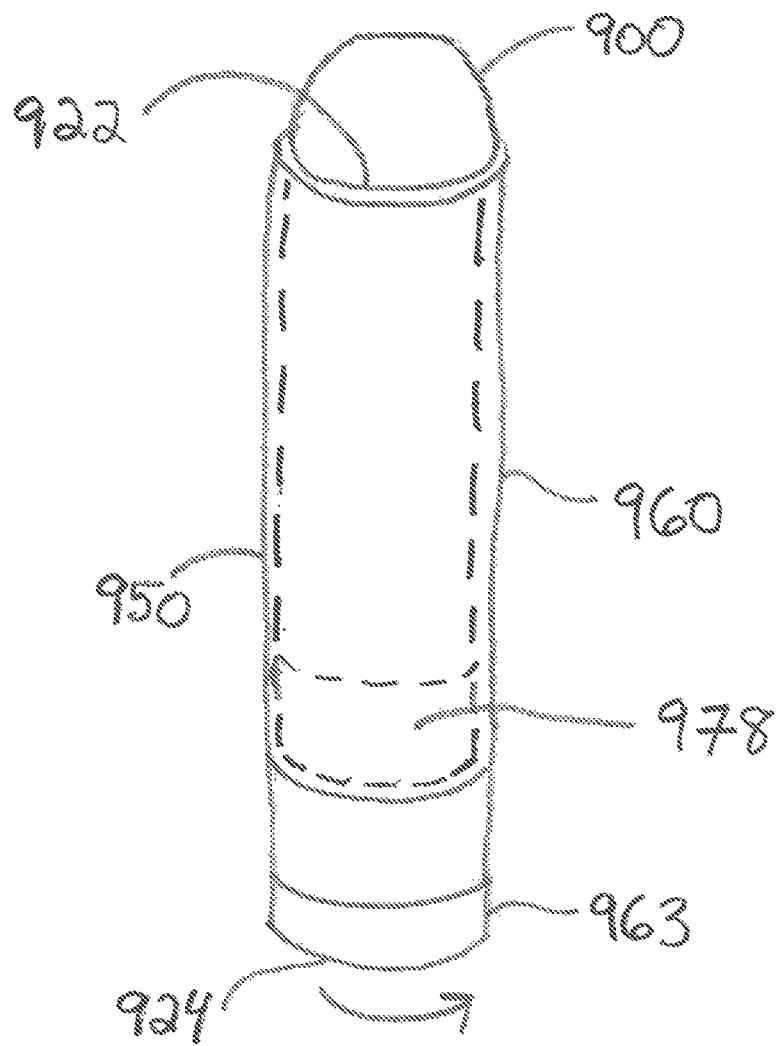
FIG. 9C shows the operation of a twisting mechanism of a stick container in accordance with an embodiment.

In a well-known manner, a user may remove cap 967, and turn twisting mechanism 963 to force one end of stick 900 to exit from open end 922 of cylindrical body 960. FIG. 9C shows the operation of a twisting mechanism of a stick container in accordance with an embodiment. Twisting mechanism 963 includes a first, rotating, portion attached to the end of cylindrical body 960 and a second portion 978 disposed within cylindrical body 960. Turning the rotating portion of twisting mechanism 963 causes second portion 978 inside the cylindrical body 960 to move within the cylindrical body and push stick 900 toward open end 922 of cylindrical body 960 (thereby causing a desired amount of the material of stick 900 to extend from open end 922). After a sufficient length of stick 900 has emerged from cylinder 960, the user may use several fingers to hold stick container 950 and rub a portion of the material of stick 900 onto a selected surface.

Figure 10:
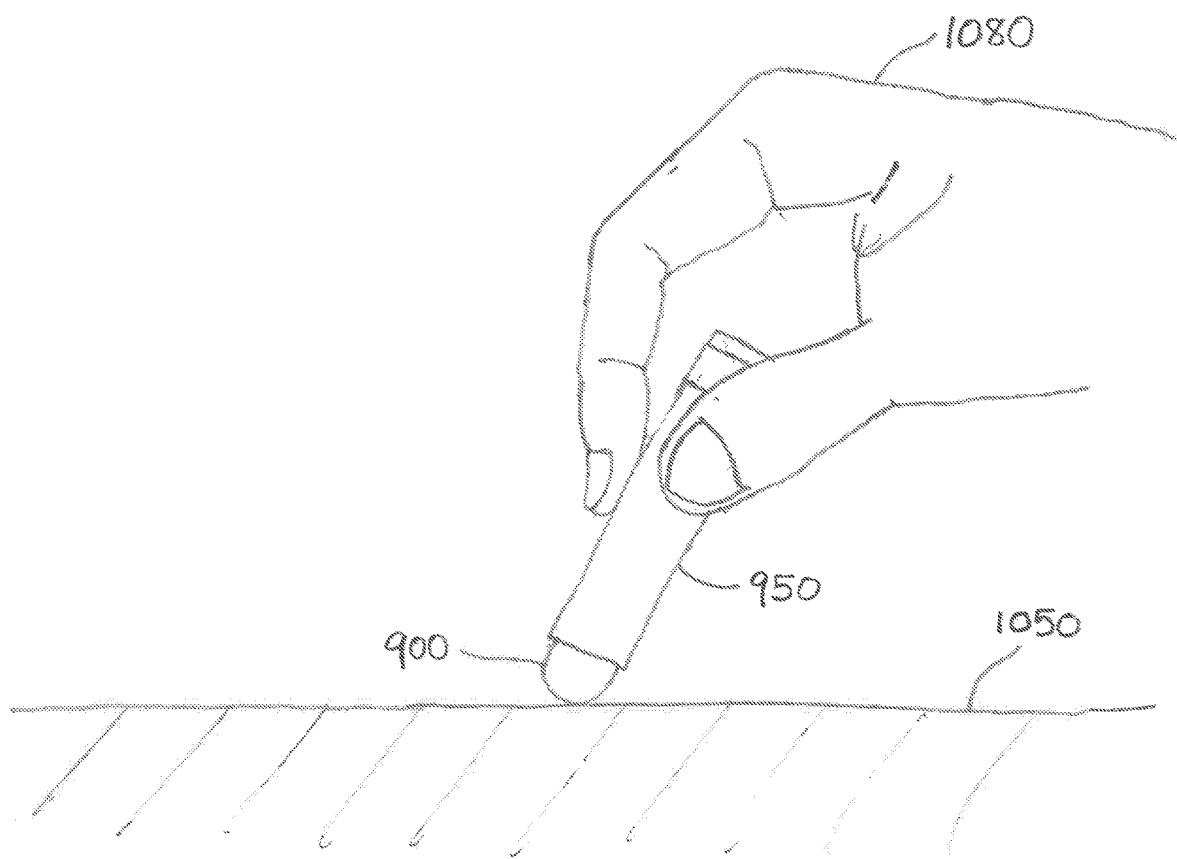
FIG. 10 shows a user employing a stick container and stick in accordance with an embodiment.

FIG. 10 shows a user's hand 1080 holding stick container 950 in accordance with an embodiment. The user positions stick container 950 in such a way as to cause stick 900 to contact a selected surface 1050, which may be, for example, a tabletop, a surface inside a drawer, a surface of a dashboard of a vehicle, a surface inside a garbage can, etc. The user then rubs stick 900 against surface 1050, causing a portion of the material of stick 900 to adhere to the surface. The material sticks to the surface and may provide desired properties, such as deodorizing, sterilizing, air freshening, etc.

Therefore, in accordance with an embodiment, a dispensing device is provided. The dispensing device includes a body having an open end, a second end, and an internal volume, a stick disposed in the internal volume of the body, the stick including a semi-solid material, and a mechanism adapted to cause a portion of the stick to extend from the open end of the body in response to an action by a user.

In one embodiment, the body has a cross-section having a shape selected from: a circle, an oval, a rectangle, a square, a triangle, and a star.

In another embodiment, the mechanism includes a first portion attached to the second end of the body, the first portion being adapted to rotate, and a second portion disposed inside the internal volume, wherein rotation of the first portion causes the second portion to move within the internal volume and push the stick toward open end.

In another embodiment, the semi-solid material includes one of a deodorizing material, an antiperspirant material, a sanitizing material, a perfume, a sterilizing material, an air freshening material, and an insect repellent material.

In another embodiment, the dispensing device includes a cap adapted to attached to and cover the open end of the body.

The stick may be uniformly composed of or formed from a semi-solid material. In another embodiment, the stick includes a plurality of blocks, wherein each block includes a first layer of aluminum foil, a second layer of an adhesive material, and a third layer of a semi-solid material. Each block is removably attached to the stick.

In accordance with another embodiment, a dispensing device includes a container comprising an open end, a stick disposed in the container, the stick comprising a plurality of blocks, each block containing a first layer of a semi-solid material and a second layer of an adhesive material, each block being detachable from the stick, and a mechanism adapted to allow a user to access and detach a selected block from the stick.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

The invention claimed is:

1. A dispensing device comprising:
    a body comprising an open end, a second end, and an internal volume;
        a stick disposed in the internal volume of the body, the stick comprising a semi-solid material;
        a mechanism adapted to cause a portion of the stick to extend from the open end of the body in response to an action by a user;
        wherein the stick comprises a plurality of blocks, wherein each block includes a first layer of the semi-solid material, a second layer of aluminum foil, and a third layer of an adhesive material;
        wherein each block is removably attached to the stick; and
        wherein the semi-solid material includes one of a deodorizing material, an antiperspirant material, a sanitizing material, a perfume, a sterilizing material, an air freshening material, and an insect repellent material.

2. The dispensing device of claim 1, wherein the body has a cross-section having a shape selected from: a circle, an oval, a rectangle, a square, a triangle, and a star.

3. The dispensing device of claim 1, wherein the mechanism comprises a first portion attached to the second end of the body, the first portion being adapted to rotate, and a second portion disposed inside the internal volume, wherein rotation of the first portion causes the second portion to move within the internal volume and push the stick toward open end.

4. The dispensing device of claim 1, further comprising a cap adapted to attached to and cover the open end of the body.

* * * * *